United States Patent [19]

Rane et al.

[11] 4,352,808
[45] Oct. 5, 1982

[54] 3-ARALKYLOXY-2,3-DIHYDRO-2-(IMIDAZOLYLMETHYL)BENZO(B)THIOPHENES AND RELATED DERIVATIVES, THEIR USE AS ANTIMICROBIALS AND PHARMACEUTICAL FORMULATIONS USEFUL THEREFORE

[75] Inventors: Dinanath F. Rane, Emerson; John J. Wright, Cedar Grove; Russell E. Pike, Stanhope, all of N.J.

[73] Assignee: Schering Corporation, Kenilworth, N.J.

[21] Appl. No.: 215,948

[22] Filed: Dec. 12, 1980

[51] Int. Cl.$^3$ .................... A01N 43/42; A01N 43/50; C07D 405/08; C07D 215/12
[52] U.S. Cl. ................... 424/258; 548/336; 548/203; 544/376; 546/274; 546/176; 424/273 R; 424/263; 424/270
[58] Field of Search .................. 548/336, 189, 203; 544/376; 546/274, 176; 260/245.5; 424/273 R, 263, 258, 270

[56] References Cited

U.S. PATENT DOCUMENTS

| | | | |
|---|---|---|---|
| 3,927,018 | 12/1975 | Houlihan | 548/336 |
| 4,036,970 | 7/1977 | Walker et al. | 548/336 |
| 4,078,071 | 3/1978 | Walker et al. | 548/336 |
| 4,267,179 | 5/1981 | Heeres et al. | 548/336 |
| 4,269,845 | 5/1981 | Worthington et al. | 548/336 |

FOREIGN PATENT DOCUMENTS 1445707  8/1973  United Kingdom ................ 548/336

*Primary Examiner*—Henry R. Jiles
*Assistant Examiner*—Robert C. Whittenbaugh
*Attorney, Agent, or Firm*—Anita W. Magatti; Mary S. King; Bruce M. Eisen

[57] ABSTRACT

3-Aralkyloxy-2,3-dihydro-2-(imidazolylmethyl(benzo(b)thiophenes and related derivatives having antifungal, antibacterial, and antiprotozoal activity are prepared by the reaction of the corresponding 2,3-dihydro-3-hydroxy-2-(imidazolylmethyl)benzo(b)thiophene or related derivative and an aralkyl halide.

Preferred compounds are those where the aralkyl function is a hetercyclic aromatic, particularly 2-chloro-3-thenyl, and where the benzene nucleus is substituted by chlorine or fluorine.

Pharmaceutical formulations comprising compounds of this invention are described, as well as the method for their use in treating microbial infections.

24 Claims, No Drawings

3-ARALKYLOXY-2,3-DIHYDRO-2-(IMIDAZOLYL-METHYL)BENZO(B)THIOPHENES AND RELATED DERIVATIVES, THEIR USE AS ANTIMICROBIALS AND PHARMACEUTICAL FORMULATIONS USEFUL THEREFORE

FIELD OF THE INVENTION

This invention relates to novel compositions-of-matter, to pharmaceutical formulations, and to methods for their use as antimicrobial agents.

More specifically, this invention relates to novel 3-aralkyloxy-2,3-dihydro-2-(imidazolylmethyl)benzo(b)-thiophenes and related derivatives which exhibit antifungal, antibacterial, and antiprotozoal activity, pharmaceutical compositions comprising said 3-aralkyloxy-2,3-dihydro-2-(imidazolylmethyl)benzo(b)thiophenes and derivatives, and to methods for their use in treating fungal, bacterial or protozoal infection.

In particular, this invention relates to 3-aralkyloxy-2,3-dihydro-2-(imidazolylmethyl)benzo(b)thiophenes and benzo(b) furans, and the corresponding 4-aralkyloxy-3-(imidazolylmethyl) thiochromans and chromans.

This invention also relates to pharmaceutical compositions comprising said 3-aralkyloxy-2,3-dihydro-2-(imidazolymethyl)benzo(b)thiophenes and related derivatives, and to the method of using said pharmaceutical compositions to elicit an antimicrobial (i.e., antibacterial, antifungal or antiprotozoal) response in a warm blooded animal having a susceptible microbial (i.e., bacterial, fungal or protozoal) infection.

GENERAL DESCRIPTION OF THE INVENTION COMPOSITION-OF-MATTER ASPECT

Included among the antimicrobially active compositions-of-matter of this invention are compounds of the formula I:

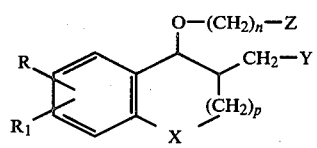

wherein
n is 0 to 4;
p is 0 to 1;
R and $R_1$ are independently hydrogen, lower alkyl, halogen, halogenated lower alkyl, nitro, or amino groups;
X is oxygen, sulfur, sulfinyl or sulfonyl;
Y is imidazole, 1,2,4-triazole, or lower alkyl and aryl derivatives of the foregoing, said aryl being a member selected from the group consisting of phenyl, halophenyl, and loweralkylphenyl;
Z is a member selected from the group consisting of alkyl, alkenyl, alkynyl, cycloalkyl, and heterocyclic aromatic groups and the lower alkyl and halogen substituted derivatives thereof, provided that when n is 0, Z is not 1-alkynyl; and where n is 1 to 4, Z is a member selected from the group consisting of phenyl, phenyl substituted by lower alkyl, halogen, or N-(N'-alkanoyl-piperazine), alkoxy, alkylthio, aryloxy, and arylthio;
and the pharmaceutically acceptable acid addition salts thereof.

As used in the specification and claims, the term "halogen" refers to fluorine, chlorine, bromine and iodine. "Lower alkyl" refers to hydrocarbon chains of 1 to 4 carbon atoms, for example methyl, ethyl, n-propyl, iso-propyl, or t-butyl groups.

Included among the substituents contemplated for the moiety "Z" are alkyl groups, straight or branched, of 1 to 10 atoms, examples of which include the aforementioned lower alkyl groups, plus n-butyl, t-butyl, n-pentyl, n-hexyl, 2-ethylpentyl, and t-decyl groups; alkoxy groups having 1–10 carbon atoms, including methoxy, ethoxy, propoxy, and decyloxy; alkylthio groups having 1–10 carbon atoms, i.e. methylthio, ethylthio, decylthio; cycloalkyl groups having 3–6 carbons, including cyclopropyl, cyclobutyl, cyclopentyl, and cyclohexyl; alkenyl groups including straight or branched chains of 3 to 10 carbons, including 1-propenyl, 2-propenyl, 2-pentenyl, 3-hexenyl, 5-octenyl, and 2-decenyl; and alkynyl groups including straight or branched chains having 3–10 carbons, for example propynyl, 2-butynyl, 2-pentynyl and 5-decynyl.

Also included for the moiety "Z" are groups such as phenyl substituted by lower alkyl, halogen, or N-(N'-alkanoylpiperazine) e.g. mono-, di-, and tri-halogenophenyls, mono-, di-, and tri-lower alkylphenyl, and the 1-acetyl-4-piperazinylphenyl and halogeno- and lower alkyl-substituted phenyl, e.g. mono-, di-, and tri-lower alkylphenyl and mono-, di-, and tri-halogenophenyl such as 4-chlorophenyl, 2,4-dichlorophenyl, 2,6-dichlorophenyl, 2,4,6-trichlorophenyl, tolyl, xylyl, and mesityl.

The alkanoyl groups contemplated in the term "N-(N'-alkanoylpiperazine)" are residues of straight or branched chain alkanoic acids having up to 6 carbon atoms, for example formyl, acetyl, or butyryl.

Aromatic heterocyclic groups contemplated for the moiety "Z" are unsaturated ring systems containing at least one hetero atom and 3 to 10 carbons in a single or fused ring system which may be substituted by halogen or lower alkyl groups, such as 2-thienyl, 3-thienyl, 2-chloro-3-thienyl, 5-chloro-2-thienyl, 2,5-dichloro-3-thienyl, pyridyl, quinolyl, thiazolyl, and furanyl.

Of the compounds of formula I, preferred are those where X is sulfur and p is 0, i.e. compounds of the following formula II, particularly the cis isomer:

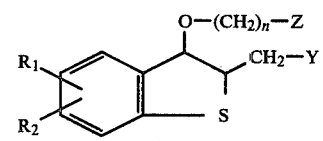

wherein $R_1$, $R_2$, Y, Z, and n are as defined in formula I. Of the compounds of formula II, particularly valuable are those where Z is a substituted phenyl or heterocyclic aromatic group. Of these, particularly preferred are compounds where Z is thienyl and Y is imidazole.

Typical compounds of formula II are:
cis-6-chloro-3-(2'-chloro-3'-thenyloxy)-2,3-dihydro-2-(1"-imidazolylmethyl)benzo(b)thiophene
cis-6-chloro-3-(2',5'-dichloro-3'-thenyloxy)-2,3-dihydro-2-(1"-imidazolylmethyl)benzo(b)thiophene
cis-6-chloro-3-(4'-chlorobenzyloxy)-2,3-dihydro-2-(1"-imidazolylmethyl)benzo(b)thiophene
cis-6-chloro-3-(2',4'-dichlorobenzyloxy)-2,3-dihydro-3-(1"-imidazolylmethyl)benzo(b)thiophene cis-5-chloro-3-(2'-chloro-3'-thenyloxy)-2,3-dihydro-2-(1''-imidazolylmethyl)benzo(b)thiophene
cis-7-chloro-3-(2'-chloro-3'-thenyloxy)-2,3-dihydro-2-(1''-imidazolylmethyl)benzo(b)thiophene
cis-5,6-dichloro-3-(2'-chloro-3'-thenyloxy)-2,3-dihydro-2-(1''-imidazolylmethyl)benzo(b)thiophene
cis-5,7-dichloro-3-(2'-chloro-3'-thenyloxy)-2,3-dihydro-2-(1''-imidazolylmethyl)benzo(b)thiophene
cis-6-trifluoromethyl-3-(2'-chloro-3'-thenyloxy)-2,3-dihydro-2-(1''-imidazolylmethyl)benzo(b)thiophene
cis-3-(4'-chlorobenzyloxy)-2,3-dihydro-2-(1''-imidazolylmethyl)benzo(b)thiophene
cis-5-chloro-3-(4'-chlorobenzyloxy)-2,3-dihydro-2-(1''-imidazolylmethyl)benzo(b)thiophene
cis-5-chloro-3-(2',4'-dichlorobenzyloxy)-2,3-dihydro-2-(1''-imidazolylmethyl)benzo(b)thiophene
cis-4,6-dichloro-3-(4'-chlorobenzyloxy)-2,3-dihydro-2-(1''-imidazolylmethyl)benzo(b)thiophene
cis-4,6-dichloro-3-(2',4'-dichlorobenzyloxy)-2,3-dihydro-2-(1''-imidazolylmethyl)benzo(b)thiophene
cis-5,6-dichloro-3-(2',4'-dichlorobenzyloxy)-2,3-dihydro-2-(1''-imidazolylmethyl)benzo(b)thiophene
cis-5-chloro-3-(2',6'-dichlorobenzyloxy)-2,3-dihydro-2-(1''-imidazolylmethyl)benzo(b)thiophene
cis-5-fluoro-3-(2'-chloro-3'-thenyloxy)-2,3-dihydro-2-(1''-imidazolylmethyl)benzo(b)thiophene
cis-6-chloro-3-(2'-chloro-5'-thenyloxy)-2,3-dihydro2-(1''-imidazolylmethyl)benzo(b)thiophene
cis-5-chloro-3-]2'-(4''-(1'''-acetyl-4'''-piperazinyl)-phenoxy)ethoxy]-2,3-dihydro-2-(1''''-imidazolylmethyl)benzo(b)thiophene
cis-6-fluoro-3-(2'-chloro-3'-thenyloxy)-2,3-dihydro-2-(1''-imidazolylmethyl)benzo(b)thiophene
cis-6-chloro-3-(3'-thenyloxy)-2,3-dihydro-2-(1''-imidazolylmethyl)benzo(b)thiophene, and
cis-6-chloro-3-(3'-picolyloxy)-2,3-dihydro-2-(1''-imidazolylmethyl)benzo(b)thiophene.

Of the foregoing, cis-6-fluoro-3-(2'-chloro-3'-thenyloxy)-2,3-dihydro-2-(1''-imidazolylmethyl)benzo(b)thiophene
cis-5-fluoro-3-(2'-chloro-3'-thenyloxy)-2,3-dihydro-2-(1''-imidazolylmethyl)benzo(b)thiophene
cis-6-chloro-3-(2'-chloro-3'-thenyloxy)-2,3-dihydro-2-(1''-imidazolylmethyl)benzo(b)thiophene and
cis-6-chloro-3-(3'-thenyloxy)-2,3-dihydro-2-(1''-imidazolylmethyl)benzo(b)thiophene are preferred.

Other typical compounds of formula I are:
cis-6-chloro-3-(2'-chloro-3'-thenyloxy)-2,3-dihydro-2-[1''-(2''-methylimidazolyl)methyl]benzo(b)thiophene
cis-6-chloro-3-(n-hexyloxy)-2,3-dihydro-2-(1'-imidazolylmethyl)benzo(b)thiophene
cis-6-chloro-3-(cyclopropylmethoxy)-2,3-dihydro-2(1'-imidazolylmethyl)benzo(b)thiophene
cis-6-chloro-3-(2',4'-dichlorobenzyloxy)-2,3-dihydro-2-(1''-imidazolylmethyl)benzo(b)thiophene-1-oxide
cis-6-chloro-2',4'-dichlorobenzyloxy)-2,3-dihydro-2-(1''-imidazolylmethyl)benzo(b)thiophene-1,1-dioxide
cis-7-chloro-3-(methylthiomethoxy)-2,3-dihydro-2-(1'-imidazolylmethyl)benzo(b)thiophene
cis-7-chloro-4-(4'-chlorobenzyloxy)-3-(1''-imidazolylmethyl)thiochroman
cis-7chloro-4-(2'-chloro-3'-thenyloxy)-3-(1''-imidazolylmethyl)thiochroman
cis-4-(2',6'-dichlorobenzyloxy)-3-(1''-imidazolylmethyl)thiochroman
cis-7-trifluoromethyl-4-(2',5'-dichloro-3'-thenyloxy)-3-(1''-imidazolylmethyl)thiochroman, and
cis-7-chloro-4-(4'-chlorobenzyloxy)-3-[1''-(2''-methylimidazolyl)methyl]thiochroman.

Also included are the analogs of the above compounds in which X is oxygen, such as the following:
cis-6-chloro-3-(2'-chloro-3'-thenyloxy)-2,3-dihydro-2-(1''-imidazolylmethyl)benzo(b)furan
cis-6-chloro-3-(2'-chloro-3'-thenyloxy)-2,3-dihydro-2-[1''-(2''-methylimidazolyl)methyl]benzo(b)furan
cis-7-chloro-4-(4'-chlorobenzyloxy)-3-(1''-imidazolylmethyl)chroman, and
cis-7-chloro-4-(2'-chloro-5'-thenyloxy)-3-(1''-imidazolylmethyl)chroman.

Compounds of formula I can exist in two isomeric forms, i.e. when p is 1, cis-3,4 or trans-3,4, and when p is 0, cis-2,3 or trans-2,3. Both forms are within the inventive concept as defined by formulae I and II, as are the individual optical isomers.

Also included within the composition-of-matter aspect of this invention are pharmaceutically acceptable acid addition salts of the compounds defined by formula I, which salts are made according to known procedures such as by neutralizing the free base with the appropriate acid, usually to about pH5. Suitable acids for this purpose include acids such as hydrochloric, sulfuric, phosphoric, hydrobromic, nitric and the like.

Compounds of this invention where X is sulfur are prepared by reacting substituted hydroxyl compounds of the formula III

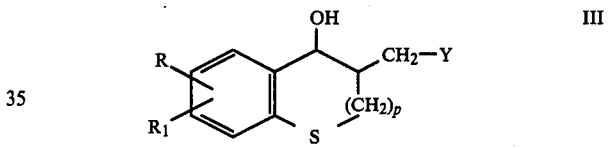

in which R, R₁, Y, and p have the meanings given above, with an alkali metal base and with a halide Z(CH₂)ₙA, in which Z and n are as defined above and A is a halogen atom, to give a compound of formula I. If desired, the resulting compound is converted into a pharmaceutically acceptable acid addition salt.

The reaction of a compound of the general formula III with an alkali metal base (for example an alkali metal hydride, alkali metal hydroxide, alkali metal amide or alkali metal alcoholate) and with a halide, Z(CH₂)ₙA, is carried out in an organic solvent, for example dimethylformamide, hexamethylphosphoric acid triamide, an aromatic hydrocarbon (e.g., benzene or toluene), an ether (e.g., diethyl ether, dioxane, tetrahydrofuran or ethylene glycol dimethyl ether), a lower alcohol, or a ketone (e.g., acetone) at a temperature within the range of 0°–100° C., and preferably within the range from 20°–60° C.

In order to increase the yield, the alkali metal base and the halide may be used in excess.

In a preferred method of preparation of compounds of formula I where X is sulfur, such as disclosed in Example 1 or 2, sodium hydride is added to a solution of a hydroxyl compound of formula III in dimethylformamide at 0°–5° C., then allowed to react at room temperature for 1 hour, followed by the addition of the halide Z(CH₂)ₙA and reaction for another hour at room temperature. The compound of formula I thereby produced is isolated and purified utilizing known techniques such as extraction, chromatography, and recrystallization.

Compounds of formula I wherein X is SO or SO$_2$ are prepared from compounds wherein X is sulfur, using oxidative procedures known in the art.

The halide starting materials, Z(CH$_2$)$_n$A, are generally known in the art or are made by procedures well known in the art. Typical halides useful in our procedure are n-hexyl chloride, allyl chloride, propargyl chloride, cyclopropylmethyl chloride, methoxymethyl chloride, methythiomethyl chloride, p-chloro-phenoxymethyl chloride, p-chloro-phenylthiomethyl chloride, and 1-[(4'-(1''-acetyl-4''-piperazinyl))phenoxy]-2-bromoethane.

Similarly, the starting materials for compounds of formula III where X is sulfur may be made by one of the following sequences of reactions, utilizing techniques known in the art:

(a) a thiochroman-4-one substituted in the benzene nucleus with R functions as defined for formula III is first converted to the corresponding bromoketone by reaction with bromine in a solvent such as ether, chloroform, or carbon tetrachloride. The bromoketone thereby formed is then converted to the corresponding bromohydrin by reaction with a reducing agent, for example, sodium borohydride, in a solvent such as a lower alcohol. The resulting bromohydrin is reacted with imidazole or a substituted imidazole in a solvent such as dimethylformamide, hexamethylphosphoric acid triamide, a lower alcohol or acetonitrile to give a compound of formula III.

(b) An aqueous solution of imidazole or a substituted imidazole is reacted with a 3-dimethylaminomethyl-thiochroman-4-one to form the corresponding 3-imidazolylmethyl (or substituted imidazolylmethyl)thiochroman-4-one which, upon reduction with a reducing agent such as sodium borohydride produces a compound of formula III as an isomeric mixture of cis and trans forms. The product may be used as a mixture or separated via conventional techniques (usually chromatography such as described in Preparation 2) to obtain the cis and trans forms free from any co-produced isomer. This procedure is a preferred method of producing compounds where p is 1.

GENERAL DESCRIPTION OF PHARMACEUTICAL COMPOSITION AND METHOD-OF-USE ASPECTS OF THE INVENTION

The present invention includes within its scope the method of eliciting an antifungal, antibacterial, or antiprotozoal response in a host object containing or subject to attack by fungi, bacteria or protozoa which comprises subjecting said host object to an antifungally, antibacterially, or antiprotozoally effective amount of a 3-aralkyloxy-2,3-dihydro-2-(imidazolylmethyl)benzo(b)thiophene or related derivatives of formula I.

The compounds of formula I exhibit antifungal activity against human and animal pathogens such as the following:
Aspergillus, Candida, Epidermophyton, Geotrichum, Microsporum, Monosporium, Pityrosporum, Rhodotorula, Saccharomyces, Trichophyton, Trichosporon, and Torulopsis, and against protozoal pathogens such as Trichomonas.

Additionally, antibacterial activity is exhibited by compounds of formula I against human and animal pathogens such as the following:

Actinomyces, Bacillus, Bacteriodes, Clostridium, Escherichia, Mycobacterium, Nocardia, Propionibacterium, Sarcina, Staphylococcus, Streptococcus, and Streptomyces.

The compounds of formula I also exhibit activity against fungi of primarily agricultural significance, such as the following:
Cladosporium, Colletotrichum, Erysiphe, Fusarium, Helminthosporium Penicillium, Peronospora, Phytophthora, Pithomyces Polyspora, Puccina, Rhizoctonia, Sclerotium, Uromyces, and Venturia, and against bacteria of primarily agricultural significance, such as: Agrobacterium, Erwinia, and Xanthemonas.

As discussed hereinabove, the preferred compounds of this invention, i.e. those of formula II, are particularly valuable as antifungal agents as demonstrated by in vivo tests in animals, e.g. a hamster Candida infection model, a guinea pig dermatophyte infection model and a mouse systemic Candida infection model. These tests indicate the compounds of this invention to be broad-spectrum antifungal agents active topically, orally and parenterally against topical dermatophyte and vaginal and systemic yeast infections.

In general, the dosage of compounds of formula I employed to combat a given fungal infection is similar to the dosage requirements of miconazole, clotrimazole, and ketoconazole, though the particular dosage level and the mode of administration will vary according to the particular host and the type and severity of the infection.

Also included in our inventive concept are pharmaceutical formulations comprising an antifungally, antibacterially or antiprotozoally effective amount of a compound of formula I in a pharmaceutically acceptable, non-toxic carrier for topical, oral or parenteral use.

Topical pharmaceutical dosage forms may be prepared according to procedures well known in the art, and may contain a variety of ingredients. The formulations for topical use include ointments, creams, lotions, powders, aerosols and sprays. Of these, ointments, lotions and creams may contain water, oils, fats, waxes, polyesters, alcohols, or polyols, plus such other ingredients as fragrances, emulsifiers and preservatives. Powders are made by mixing the active ingredient with a readily available, inert, pulverous distributing agent, such as talcum, calcium carbonate, tricalcium phosphate, or boric acid. Aqueous suspensions of the above powders may also be made. Solutions or emulsions may also be prepared using inert solvents which are preferably nonflammable, odorless, colorless, and non-toxic, for example vegetable oils, isopropanol, dimethyl sulfoxide, hydrogenated naphthalenes, and alkylated naphthalenes. Similarly, aerosol or non-aerosol sprays may be prepared using solutions or suspensions in appropriate solvents, e.g. difluorodichloromethane for aerosols.

In the case of topical formulations, e.g. ointments, creams, lotions, powders, or sprays, the formulation will contain about 0.1 to 3 grams of compound of formula I per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intavenously, intramuscularly, or subcutaneously are usually in the form of a sterile solution, and may contain salts or glucose to make the solution isotonic.

In addition to pharmeceutical uses, the compounds of this invention also have agricultural and industrial significance. In agricultural applications, the compounds may be applied directly to plants or soil. The carriers may be powders, such as talc, mica, or clay, or sprays, such as aqueous solutions with or without a solid carrier and a wetting agent. Industrially, the compounds may be used to disinfect glassware, medical equipment, and the like, by rinsing, contacting or impregnating the infected surface with compound in a suitable carrier. Additionally, the compounds may be used to prevent growth of fungi in paints.

The following formulations are to exemplify some of the dosage forms in which the antimicrobial agents of the invention may be employed. In each, the active ingredient is designated by the term "Drug" which is meant to indicate one of the following compounds:

cis-6-fluoro-3-(2'-chloro-3'-thenyloxy)-2,3-dihydro-2-(1''-imidazolylmethyl)benzo(b)thiophene;
cis-5-fluoro-3-(2'-chloro-3'-thenyloxy)-2,3-dihydro-2-(1''-imidazolylmethyl)benzo(b)thiophene;
cis-6-chloro-3-(2'-chloro-3'-thenyloxy)-2,3-dihydro-2-(1''-imidazolylmethyl)benzo(b)thiophene; and
cis-6-chloro-3-(3'-thenyloxy)-2,3-dihydro-2-(1''-imidazolylmethyl)benzo(b)thiophene.

It will be appreciated, however, that each of these compounds may be replaced by equally effective quantities of other compounds defined by formula I.

| FORMULATION I | |
|---|---|
| Tablet A | 7.50 mg. tab. |
| Drug | 7.50 mg. |
| Lactose, Anhydrous | 114.14 mg. |
| Starch (Sta-Rx 1500) | 54.66 mg. |
| Sodium lauryl sulfate | 5.00 mg. |
| Microcrystalline cellulose | 16.44 mg. |
| Silica gel | 0.41 mg. |
| Magnesium stearate | 1.85 mg. |
| Water (Evaps.) | (0.05) mg. |

Procedure:

Blend the drug, lactose, and starch. Granulate with aqueous sodium lauryl sulfate solution. Dry the granulation, mill, and blend granules with microcrystalline cellulose, silica gel, and magnesium stearate. Compress into tablets.

| FORMULATION II | |
|---|---|
| Tablet B | 125.00 mg. tab. |
| Drug | 125.00 mg. |
| Polyethylene glycol 6000 | 100.00 mg. |
| Sodium lauryl sulfate | 6.25 mg. |
| Corn starch | 30.00 mg. |
| Lactose, anhydrous | 87.25 mg. |
| Magnesium stearate | 1.50 mg. |

Procedure:

Heat the polyethylene glycol 6000 to 70°-80° C. Mix the drug, sodium lauryl sulfate, corn starch, and lactose into the liquid and allow the mixture to cool. Pass the solidified mixture through a mill. Blend granules with magnesium stearate and compress into tablets.

| FORMULATION III | |
|---|---|
| Capsule A | 25 mg. cap. |
| Drug | 25.00 mg. |
| Microcrystalline cellulose | 312.00 mg. |
| Sodium lauryl sulfate | 5.00 mg. |
| Corn starch | 90.00 mg. |
| Hydroxypropyl Methylcellulose | 13.50 mg. |
| Magnesium stearate | 4.50 mg. |
| Water (Evaps) | (Evaps.) |

Procedure:

Mix the drug, microcrystalline cellulose, sodium lauryl sulfate, and corn starch, and granulate with aqueous hydroxypropyl methylcellulose. Dry and mill the granulation, then mix with magnesium stearate and fill capsules with the mixture.

| FORMULATION IV | |
|---|---|
| Capsule B | 5.00 mg. caps. |
| Drug | 5.00 mg. |
| Sodium lauryl sulfate | 25.00 mg. |
| Corn starch | 310.00 mg. |

Procedure:

Mix the drug, sodium lauryl sulfate, and corn starch. Fill capsules with mixture.

| FORMULATION V | |
|---|---|
| Injection | mg/ml |
| Drug | 10.00 |
| Methylparaben | 1.30 |
| Propylparaben | 0.20 |
| Sodium bisulfite | 3.20 |
| Disodium edetate | 0.10 |
| Sodium sulfate | 2.60 |
| Water for injection q.s. ad | 1.0 ml. |

Procedure:

Dissolve parabens in a portion (approximately 85% of the final volume) of the water for injection at 65°-70° C. Cool to 25°-35° C., then charge and dissolve the sodium bisulfite, disodium edetate, and sodium sulfate. Charge and dissolve the drug. Bring the solution to the final volume by adding the water for injection, filter the solution through a 0.22 membrane, and fill into the appropriate containers. Sterilize the units by autoclaving.

| FORMULATION VI | |
|---|---|
| Injectable Suspension | mg/ml |
| Drug | 10.00 |
| Benzyl alcohol | 9.0 |
| Methylparaben | 1.8 |
| Propylparaben | 0.2 |
| Sodium carboxymethylcellulose | 5.0 |
| Polyethylene glycol 4000 | 10.0 |
| Povidone | 5.0 |
| Sodium citrate | 15.0 |
| Disodium edetate | 0.1 |
| Water for injection q.s. ad | 1.0 ml. |

Procedure:

Dissolve parabens in a portion of water for injection at 65°–70° C. Cool to 25°–35° C., charge and dissolve the benzyl alcohol, sodium citrate, disodium edetate, PEG 4000, povidone, and sodium carboxymethylcellulose, then filter the solution and sterilize by autoclaving. Prepare a slurry of the sterile drug, pass it through a colloid mill, mix it well with the autoclaved solution from above, and pass it through the colloid mill again. Bring the solution to the final volume by adding the water for injection and fill into sterile containers.

FORMULATION VII
Sterile Powder for Injection

| Drug (sterile powder) | 20 mg. |
|---|---|
| Water for injection* | 10–200 ml. |

*Add sterile or bacteriostatic water for injection, USP water for reconstitution.

FORMULATION VIII

| Cream | Amounts in (mg) | | |
|---|---|---|---|
| | A | B | C |
| Drug | 0.5 | 5.0 | 10.0 |
| Sorbitan Monostearate | 20.0 | 20.0 | 20.0 |
| Polysorbate 60 | 15.0 | 15.0 | 15.0 |
| Spermaceti Synthetic | 30.0 | 30.0 | 30.0 |
| Cetostearyl Alcohol | 100.0 | 100.0 | 100.0 |
| Octyl Dodecanol | 135.0 | 135.0 | 135.0 |
| Benzyl Alcohol | 10.0 | 10.0 | 10.0 |
| Purified Water | to make 1 gram | 1 gram | 1 gram |

Procedure:

Heat the sorbitan monostearate, 95% of the polysorbate 60, synthetic spermaceti, cetostearyl alcohol, and octyl dodecanol to 70° C. Dissolve the benzyl alcohol in 90% of the purified water heated to 75° C. Add the aqueous solution to the melted waxes and stir while cooling to 40° C. Dissolve the remaining portion of the polysorbate 60 in the remaining portion of water, add the drug and pass the slurry through a colloid mill. Add the slurry to the wax mixture until cool.

FORMULATION IX

| Gel | A | B | C |
|---|---|---|---|
| Drug | 0.5 | 5.0 | 10.0 |
| Butylated Hydroxytoluene | 5.0 | 5.0 | 5.0 |
| Carbomer 940 | 15.0 | 15.0 | 15.0 |
| Propylene Glycol | 300.0 | 300.0 | 300.0 |
| Sodium Hydroxide | 0.6 | 0.6 | 0.6 |
| Polyethylene Glycol 400 | to make 1 gram | 1 gram | 1 gram |

Procedure:

Dissolve the drug and the butylated hydroxytoluene in 90% of the propylene glycol and the polyethylene glycol 400. Disperse the carbomer in the drug solution. Add the sodium hydroxide, previously dissolved in the remaining portion of propylene glycol, and stir until homogeneous.

FORMULATION X

| Ointment | A | B | C |
|---|---|---|---|
| Drug | 0.5 | 5.0 | 10.0 |
| Mineral Oil | 50.0 | 50.0 | 50.0 |
| White Petrolatum | to make 1 gram | 1 gram | 1 gram |

Procedure:

Heat the petrolatum to 70° C. Add the drug to the mineral oil and pass the slurry through a colloid mill. Add the slurry to the melted petrolatum and mix while cooling to room temperature.

FORMULATION XI

| Lotion | A | B | C |
|---|---|---|---|
| Drug | 0.5 | 5.0 | 10.0 |
| Sorbitan Monostearate | 2.0 | 2.0 | 2.0 |
| Polysorbate 60 | 30.0 | 30.0 | 30.0 |
| Cetyl Esters Wax | 30.0 | 30.0 | 30.0 |
| Cetostearyl Alcohol | 40.0 | 40.0 | 40.0 |
| Octyl Dodecanol | 40.0 | 40.0 | 40.0 |
| Benzyl Alcohol | 20.0 | 20.0 | 20.0 |
| Purified Water | to make 1 gram | 1 gram | 1 gram |

Procedure:

Prepare the lotion in a manner similar to that described above for the cream in FORMULATION VIII.

FORMULATION XII

| Spray Solution | Amounts in (mg) | | |
|---|---|---|---|
| | A | B | C |
| Drug | 0.5 | 5.0 | 10.0 |
| Propylene Glycol | 200.0 | 200.0 | 200.0 |
| Lanoxol AWS | 5.0 | 5.0 | 5.0 |
| Alcohol | 300.0 | 300.0 | 300.0 |
| Purified Water | to make 1 gram | 1 gram | 1 gram |

Procedure:

Dissolve the drug and lanoxol in the propylene glycol and alcohol. Add water and mix until homogeneous.

FORMULATION XIII

| Powder | A | B | C |
|---|---|---|---|
| Drug | 0.5 | 5.0 | 10.0 |
| Starch | 100.0 | 100.0 | 100.0 |
| Talc | to make 1 gram | 1 gram | 1 gram |

Procedure:

Mill the drug with the starch. Add milled drug—starch mixture to talc and mix until uniform.

The processes described hereinabove are illustrated in detail in the Preparations and Examples hereinbelow which should not be construed as limiting the invention.

PREPARATION 1

CIS-2,3-DIHYDRO-3-HYDROXY-2-(1'-IMIDAZOLYLMETHYL)-BENZO(b)THIOPHENES (A) Cis-6-Chloro-2,3-Dihydro-3-Hydroxy-2-(1'-Imidazolylmethyl)benzo(b)thiophene (1) 3-Bromo-7-Chlorothiochroman-4-One Dissolve 7-chlorothiochroman-4-one (10 gms., 50.3 mmols) in chloroform (100 ml.) and cool the solution to 0°–5° C. Add bromine (2.60 ml., 50.3 mmols) dropwise over a 10-minute period. Stir the reaction mixture at room temperature for one hour, then add chloroform (100 ml.) and extract with 10% aqueous sodium sulfite (100 ml.) followed by water (200 ml.). Dry the chloroform solution over anhydrous magnesium sulfate, filter and evaporate in vacuo to a residue. Recrystallize the residue from cyclohexane to give 3-bromo-7-chlorothiochroman-4-one, m.p. 109°–110° C.

(2) 3-Bromo-7-Chlorothiochroman-4-ol

Suspend 3-bromo-7-chlorothiochroman-4-one (59.6 gms., 215 mmols) in methanol (500 ml.), cool to 0.5° C., and with stirring add sodium borohydride (8.18 gms., 215 mmols) in three portions. Continue stirring the reaction mixture at room temperature for three hours, then pour into ice water (4 liters) and extract with chloroform (2 liters). Dry the chloroform solution over anhydrous magnesium sulfate, filter and evaporate in vacuo to a residue. Triturate the residue with chloroform/hexane to give 3-bromo-7-chlorothiochroman-4-ol, m.p. 141°–142° C.

(3) Cis-6-Chloro-2,3-Dihydro-3-Hydroxy-2-(1'-Imidazolylmethyl)benzo(b)thiophene

Add 3-bromo-7-chlorothiochroman-4-ol (5.27 gms., 18.8 mmols) and imidazole (12.8 gms., 188 mmols) to acetonitrile (100 ml.), and heat at reflux temperature for 4 hours. Pour the reaction mixture into water (500 ml.), and extract with chloroform (500 ml.). Wash the organic layer with water (500 ml.), dry the organic layer over anhydrous magnesium sulfate, filter and evaporate in vacuo. Triturate the resultant residue with anhydrous ether, filter and recrystallize from acetonitrile to give cis-6-chloro-2,3-dihydro-3-hydroxy-2-(1'-imidazolylmethyl)benzo(b)thiophene.

(B) In the procedure of above Preparation 1A(1-3), substitute for the starting compound, i.e., 7-chlorothiochroman-4-one, an equivalent quantity of each of the following:
(a) thiochroman-4-one,
(b) 6-chlorothiochroman-4-one,
(c) 8-chlorothiochroman-4-one,
(d) 5,7-dichlorothiochroman-4-one,
(e) 6,7-dichlorothiochroman-4-one,
(f) 6,8-dichlorothiochroman-4-one,
(g) 7-trifluoromethylthiochroman-4-one, to obtain, respectively,
(a) cis-2,3-dihydro-3-hydroxy-2-(1'-imidazolylmethyl)-benzo(b)-thiophene,
(b) cis-5-chloro-2,3-dihydro-3-hydroxy-2-(1'-imidazolylmethyl)-benzo(b)thiophene,
(c) cis-7-chloro-2,3-dihydro-3-hydroxy-2-(1'-imidazolylmethyl)-benzo(b)thiophene,
(d) cis-4,6-dichloro-2,3-dihydro-3-hydroxy-2-(1'-imidazolylmethyl)benzo(b)thiophene,
(e) cis-5,6-dichloro-2,3-dihydro-3-hydroxy-2-(1'-imidazolylmethyl)benzo(b)thiophene,
(f) cis-5,7-dichloro-2,3-dihydro-3-hydroxy-2-(1'-imidazolylmethyl)benzo(b)thiophene,
(g) cis-6-trifluoromethyl-2,3-dihydro-3-hydroxy-2-(1'-imidazolylmethyl)benzo(b)thiophene.

PREPARATION 2

3-(1'-IMIDAZOLYLMETHYL)THIOCHROMANOLS (A) 7-Chloro-3-(1'-Imidazolylmethyl)thiochroman-4-ol (1) 7-Chloro-3-(1'-Imidazolylmethyl)thiochroman-4-One Dissolve imidazole (25.8 gms., 380 mmols) in water (100 ml.) and add 7-chloro-3-(dimethylaminomethyl)-thiochroman-4-one hydrochloride (11.1 gms., 38.0 mmols). Stir the reaction mixture overnight at room temperature, then add water (1 liter) and extract with chloroform (500 ml.). Wash the chloroform solution with 2 liter portions of water, dry over anhydrous magnesium sulfate, filter and evaporate in vacuo to a residue. Chromatograph the residue on a silica gel column eluting with chloroform. Combine the like eluates as determined by thin layer chromatography and evaporate in vacuo to a residue comprising 7-chloro-3-(1'-imidazolylmethyl)thiochroman-4-one. Further purify by recrystallization from chloroform/hexane, m.p. 104°–105° C.

(2) Dissolve 7-chloro-3-(1'-imidazolylmethyl)thiochroman-4-one (5.0 gms., 17.9 mmols) in methanol (100 ml.), cool the solution to 0°–5° C., and add with stirring sodium borohydride (0.51 gms., 13.4 mmols). Stir the reaction mixture overnight at room temperature and evaporate in vacuo. Add water (100 ml.) to the resultant residue and stir for 30 minutes. Filter and wash the resultant residue with water (2×200 ml.) and chromatograph on a silica gel column eluting with chloroform/methanol/ammonium hydroxide (97:3:0.1). Combine the like fractions as determined by thin layer chromatography and evaporate the combined like eluates to give 2 isolated products, namely,
(a) cis-7-chloro-3-(1'-imidazolylmethyl)thiochroman-4-ol, which, after further purification by recrystallization from ethanol has a melting point of 210°–212° C., and
(b) trans-7-chloro-3-(1'-imidazolylmethyl)-thiochroman-4-ol, which, after further purification by recrystallization from ethanol has a melting point of 135° C.

(B) In the procedure of Preparation 2A, by substituting for the starting compound, i.e., 7-chloro-3-(dimethylaminomethyl)thiochroman-4-one hydrochloride, and equivalent quantity of each of the following:
(a) 3-(dimethylaminomethyl)thiochroman-4-one hydrochloride,
(b) 6-chloro-3-(dimethylaminomethyl)thiochroman-4-one hydrochloride,
(c) 8-chloro-3-(dimethylaminomethyl)thiochroman-4-one hydrochloride,
(d) 5,7-dichloro-3-(dimethylaminomethyl)thiochroman-4-one hydrochloride,
(e) 6,7-dichloro-3-(dimethylaminomethyl)thiochroman-4-one hydrochloride,
(f) 6,8-dichloro-3-(dimethylaminomethyl)thiochroman-4-one hydrochloride, (g) 7-trifluoromethyl-3-(dimethylaminomethyl)thiochroman-4-one hydrochloride.

There is obtained, upon reaction with imidazole in the manner of Preparation 2A(1), the corresponding 3-(1'-imidazolylmethyl)thiochroman-4-one derivative of each of the foregoing, which, upon reaction with sodium borohydride according to the preparation of 2A(2), yields the corresponding 4-hydroxyl derivative which, upon purification via chromatography in the described manner, is separated into their respective cis and trans isomers, i.e., (a) cis-3-(1'-imidazolylmethyl)thiochroman-4-ol,
(b) cis-6-chloro-3-(1'-imidazolylmethyl)thiochroman-4-ol,
(c) cis-8-chloro-3-(1'-imidazolylmethyl)thiochroman-4-ol,
(d) cis-5,7-dichloro-3-(1'-imidazolylmethyl)thiochroman-4-ol,
(e) cis-6,7-dichloro-3-(1'-imidazolylmethyl)thiochroman-4-ol,
(f) cis-6,8-dichloro-3-(1'-imidazolymethyl)thiochroman-4-ol,
(g) cis-7-trifluoromethyl-3-(1'-imidazolylmethyl)thiochroman-4-ol, and the trans-isomers thereof.

PREPARATION 3

1-[(4'-1"-ACETYL-4"-PIPERAZINYL)PHENOXY]-2-BROMOETHANE

Dissolve 1-acetyl-4-(4'-hydroxyphenyl)piperazine (15.0 gms., 58.5 mmols) and potassium hydroxide (3.28 gms., 58.5 mmols) in absolute ethanol (500 ml.). Add ethylenedibromide (50.4 ml., 585 mmols) and reflux the mixture for two hours. Add another portion of potassium hydroxide (3.28 gms., 58.5 mmols) and reflux again for two hours; repeat this last step two more times. Evaporate the ethanol in vacuo. Dissolve the resultant residue in chloroform (1 l.) and extract with water (1 l.). Dry the chloroform solution over anhydrous magnesium sulfate, evaporate the chloroform, and chromatograph the resultant residue on silica gel, eluting with chloroform. Combine the like fractions as determined by thin layer chromatography and evaporate the combined eluates to give 1-[(4'-(1"-acetyl-4"-piperazinyl))-phenoxy]-2-bromoethane.

PREPARATION 4

5-CHLORO-2,3-DIHYDRO-3-HYDROXY-2-(1'-IMIDAZOLYLMETHYL) BENZO(b)FURAN (A) 5-chloro-2-(1'-Imidazolylmethyl)coumaran-3-one Dissolve imidazole (37.44 gms., 550 mmols) in water (200 ml.) and add 5-chloro-2-(dimethylaminomethyl)-coumaran-3-one hydrochloride (25 gms., 55 mmols). Stir the reaction mixture overnight at room temperature, then add water (2 liters) and extract with chloroform (1 liter). Wash the chloroform solution with another 2 liter portion of water, dry over anhydrous magnesium sulfate, filter and evaporate in vacuo to give 5-chloro-2-(1'-imidazolylmethyl)coumaran-3-one.

(B)
5-chloro-2,3-dihydro-3-hydroxy-2-(1'-Imidazolylmethyl)benzo(b)furan

Dissolve 5-chloro-2-(1'-imidazolylmethyl)coumaran-3-one (10 gms., 21 mmols.) in methanol (100 ml.), cool the solution to 0°–5° C. and add sodium borohydride (1.0 gms., 26.4 mmols.). Stir the reaction mixture overnight at room temperature and evaporate the methanol in vacuo. Add water (200 ml.) to the resultant residue and stir for 30 minutes. Filter and wash the resultant residue with water to give 5-chloro-2,3-dihydro-3-hydroxy-2-(1'-imidazolylmethyl)benzo(b)furan.

PREPARATION 5

Subject equivalent quantities of each of 7-fluorothiochroman-4-one and 8-fluoro-thiochroman-4-one to the series of reactions described in Preparation 1A(1-3) to obtain cis-6-fluoro-2,3-dihydro-3-hydroxy-2-(1'-imidazolylmethyl)benzo(b) thiophene and cis-7-fluoro-2,3-dihydro-3-hydroxy-2-(1'-imidazolylmethyl)benzo(b)thiophene.

EXAMPLE 1

CIS-3-CHLOROTHENYLOXY (OR CHLOROBENZYLOXY)-2,3-DIHYDRO-2-(1"-IMIDAZOLYLMETHYL)BENZO(b)THIOPHENES

A.

Cis-6-Chloro-3-(2'-Chloro-3'-Thenyloxy)-2,3-Dihydro-2-(1"-Imidazolylmethyl)Benzo(b)Thiophenes To a solution of cis-6-chloro-2,3-dihydro-3-hydroxy-2-(1"-imidazolylmethyl)benzo(b)thiophene (2.00 gms., 7.50 mmols) in dry dimethylformamide (20 ml.) cooled to 0°–5° C., add sodium hydride (50% dispersion, 0.40 gms., 8.25 mmols) and stir at room temperature for one hour. Add 2-chloro-3-thenyl bromide (1.75 gms., 8.25 mmols) and stir at room temperature for another hour. Pour the reaction mixture into ether (500 ml.) and extract with three 500 ml. portions of water. Dry the ether solution over anhydrous magnesium sulfate, filter and evaporate in vacuo. Chromatograph the resultant residue on silica gel eluting with chloroform. Combine the like eluates as determined by thin layer chromatography and evaporate in vacuo and recrystallize the resultant residue from cyclohexane to obtain cis-6-chloro-3-(2'-chloro-3'-thenyloxy)-2,3-dihydro-2-(1"-imidazolylmethyl)-benzo(b)thiophene, m.p. 99°–101° C.

B. In the procedure of Example 1A, instead of 2-chloro-3-thenylbromide, utilize an equivalent quantity of each of the following reagents:

(a) 2,5-dichloro-3-thenyl bromide,
(b) 4-chlorobenzyl chloride,
(c) 2,4-dichlorobenzyl chloride, to obtain, respectively,
(d) cis-6-chloro-3-(2',5'-dichloro-3'-thenyloxy)-2,3-dihydro-2-(1"-imidazolylmethyl)benzo(b)thiophene,
cis-6-chloro-3-(4'-chlorobenzyloxy)-2,3-dihydro-2-(1"-imidazolylmethyl)benzo(b)thiophene, and
cis-6-chloro-3-(2', 4'-dichlorobenzyloxy)-2,3-dihydro-2-(1"-imidazolylmethyl)benzo(b)thiophene.

C. Treat each of the cis-2,3-dihydro-3-hydroxy-2-(1"-imidazolylmethyl)benzo(b)thiophenes prepared in Preparation 1B with 2-chloro-3-thenylbromide in a manner similar to that described in Example 1A to obtain, respectively, (a) cis-3-(2'-chloro-3'-thenyloxy)-2,3-dihydro-2-(1"-imidazolylmethyl)benzo(b)thiophene,
(b) cis-5-chloro-3-(2'-chloro-3'-thenyloxy)-2,3-dihydro-2-(1"-imidazolylmethyl)benzo(b)thiophene,
(c) cis-7-chloro-3-(2'-chloro-3'-thenyloxy)-2,3-dihydro-2-(1"-imidazolylmethyl)benzo(b)thiophene,
(d) cis-4,6-dichloro-3-(2'-chloro-3'-thenyloxy)-2,3-dihydro-2-(1"-imidazolylmethyl)benzo(b)thiophene,
(e) cis-5,6-dichloro-3-(2'-chloro-3'-thenyloxy)-2,3-dihydro-2-(1"-imidazolylmethyl)benzo(b)thiophene, (f) cis-5,7-dichloro-3-(2'-chloro-3'thenyloxy)-2,3-dihydro-2-(1''-imidazolylmethyl)benzo(b)thiophene, (g) cis-6-trifluoromethyl-3-(2'-chloro-3'-thenyloxy)-2,3-dihydro-2-(1''-imidazolylmethyl)benzo(b)thiophene.

D. Similarly, treat each of the cis-2,3-dihydro-3-hydroxy-(1''-imidazolylmethyl)benzo(b)thiophenes prepared in Preparation 1B with each of the three reagents listed in Example 1B to obtain respectively, (a)(1) cis-3-(2', 5'-dichloro-3-thenyloxy)-2,3-dihydro-2-(1''-imidazolylmethyl)benzo(b)thiophene, (2) cis-3-(4'-chlorobenzyloxy)-2,3-dihydro-2-(1''-imidazolylmethyl)benzo(b)thiophene, (3) cis-3-(2',4'-dichlorobenzyloxy)-2,3-dihydro-2-(1''imidazolylmethyl)benzo(b)thiophene;

(b)(1) cis-5-chloro-3-(2',5'-dichloro-3'-thenyloxy)-2,3-dihydro(1''-imidazolylmethyl)benzo(b)thiophene, (2) cis-5-chloro-3-(4'-chlorobenzyloxy)-2,3-dihydro-2-(1''-imidazolylmethyl)benzo(b)thiophene, (3) cis-5-chloro-3-(2',4'-dichlorobenzyloxy)-2,3-dihydro-2-(1''-imidazolylmethyl)benzo(b)thiophene;

(c)(1) cis-7-chloro-3-(2',5'-dichloro-3'-thenyloxy)-2,3-dihydro-2-(1''-imidazolylmethyl)benzo(b)thiophene, (2) cis-7-chloro-3-(4'-chlorobenzyloxy)-2,3-dihydro-2-(1''-imidazolylmethyl)benzo(b)thiophene, (3) cis-7-chloro-3-(2',4'-dichlorobenzyloxy)-2,3-dihydro-2-(1''-imidazolylmethyl)benzo(b)thiophene;

(d)(1) cis-4,6-dichloro-3-(2',5'-dichloro-3'-thenyloxy)-2,3-dihydro-2-(1''-imidazolylmethyl)benzo(b)thiophene, (2) cis-4,6-dichloro-3-(4'-chlorobenzyloxy)-2,3-dihydro-2-(1''-imidazolylmethyl)benzo(b)thiophene, (3) cis-4,6-dichloro-3-(2',4'-dichlorobenzyloxy)-2,3-dihydro-2-(1''-imidazolylmethyl)benzo(b)thiophene;

(e)(1) cis-5,6-dichloro-3-(2',5'-dichloro-3'-thenyloxy)-2,3-dihydro-2-(1''-imidazolylmethyl)benzo(b)thiophene, (2) cis-5,6-dichloro-3-(4'-chlorobenzyloxy)-2,3-dihydro-2-(1''-imidazolylmethyl)benzo(b)thiophene, (3) cis-5,6-dichloro-3-(2',4'-dichlorobenzyloxy)-2,3-dihydro-2-(1''-imidazolylmethyl)benzo(b)thiophene;

(f)(1) cis-5,7-dichloro-3-(2',5'-dichloro-3'-thenyloxy)-2,3-dihydro-2-(1''-imidazolylmethyl)benzo(b)thiophene, (2) cis-5,7-dichloro-3-(4'-chlorobenzyloxy)-2,3-dihydro-2-(1''-imidazolylmethyl)benzo(b)thiophene, (3) cis-5,7-dichloro-3-(2',4'-dichlorobenzyloxy)-2,3-dihydro-2-(1''-imidazolylmethyl)benzo(b)thiophene;

(g)(1) cis-6-trifluoromethyl-3-(2',5'-dichloro-3'-thenyloxy)-2,3-dihydro-2-(1''-imidazolylmethyl)benzo(b)thiophene, (2) cis-6-trifluoromethyl-3-(4'-chlorobenzyloxy)-2,3-dihydro-2-(1''-imidazolylmethyl)benzo(b)thiophene, (3) cis-6-trifluoromethyl-3-(2',4'-dichlorobenzyloxy)-2,3-dihydro-2-(1''-imidazolylmethyl)benzo(b)thiophene.

E. Treat each of cis-6-fluoro-2,3-dihydro-3-hydroxy-2-(1'-imidaziolylmethyl)benzo(b)thiophene and cis-5-fluoro-2,3-dihydro-3-hydroxy-2-(1'-imidazolylmethyl)-benzo(b)thiophene prepared in Preparation 5 in a manner described in each of Examples 1A and 1B to obtain, respectively:

(a)(1) cis-6-fluoro-3-(2'-chloro-3'-thenyloxy)-2,3-dihydro-2-(1''-imidazolylmethyl)benzo(b)thiophene, (2) cis-6-fluoro-3-(2',5'-dichloro-3'-thenyloxy)-2,3-dihydro-2-(1''-imidazolylmethyl)benzo(b)thiophene, (3) cis-6-fluoro-3-(4'-chlorobenzyloxy)-2,3-dihydro-2-(1''-imidazolylmethyl)benzo(b)thiophene, (4) cis-6-fluoro-3-(2',4'-dichlorobenzyloxy)-2,3-dihydro-2-(1''-imidazolylmethyl)benzo(b)thiophene, (b)(1) cis-5-fluoro-3-(2'-chloro-3'-thenyloxy)-2,3-dihydro-2-(1''-imidazolylmethyl)benzo(b)thiophene, (2) cis-5-fluoro-3-(2',5'-dichloro-3'-thenyloxy)-2,3-dihydro-2-(1''-imidazolylmethyl)benzo(b)thiophene, (3) cis-5-fluoro-3-(4'-chlorobenzyloxy)-2,3-dihydro-2-(1''-imidazolylmethyl)benzo(b)thiophene, (4) cis-5-fluoro-3-(2',4'-dichlorobenzyloxy)-2,3-dihydro-2-(1''-imidazolylmethyl)benzo(b)thiophene.

EXAMPLE 2

4-CHLOROBENZYLOXY (OR CHLOROTHENYLOXY)-3-(1'-IMIDAZOLYLMETHYL)THIOCHROMANS

A.

Cis-7-Chloro-4-(4'-Chlorobenzyloxy)-3-(1''-Imidazolylmethyl)Thiochroman

Stir a mixture of cis-7-chloro-3-(1'-imidazolylmethyl)-thiochroman-4-ol (1.59 gms., 5.66 mols) and sodium hydride (50% dispersion (0.34 gms., 7.0 mmols) in dry dimethylformamide (10 ml.) at room temperature for one hour. Add p-chlorobenzyl chloride (1.13 gms., 7.0 mmols) and stir at room temperature for one hour. Pour into chloroform (100 ml.) and extract with three 100 ml. portions of water. Dry the chloroform solution over anhydrous magnesium sulfate, evaporate in vacuo and chromatograph the resultant residue on a silica gel column eluting with chloroform. Evaporate the combined eluates to obtain a residue comprising cis-7-chloro-4-(4'-chlorobenzyloxy)-3-(1''-imidazolylmethyl)thiochroman. To prepare the nitrate salt, dissolve the gummy residue in anhydrous ether (250 ml.) and added dropwise a solution of nitric acid in 2-propanol until precipitation is complete. Filter the resultant precipitate of cis-7-chloro-4-(4'-chlorobenzyloxy)-3-(1''-imidazolylmethyl)thiochroman nitrate and recrystallize from ethyl acetate/hexane, m.p. 135°–137° C.

B.

Trans-7-Chloro-4-(4'-Chlorobenzyloxy)-3-(1''-Imidazolylmethyl)Thiochroman

Stir a mixture of trans-7-chloro-3-(1'-imidazolylmethyl)-thiochroman-4-ol (0.5 gms., 1.78 mmols) and sodium hydride (50% dispersion in oil) (0.11 gms., 2.29 mmols) in dry dimethylformamide (10 ml.) at room temperature for one hour. Add p-chlorobenzyl chloride (0.36 gms., 2.23 mmols) and stir the reaction mixture at room temperature for one hour. Pour into chloroforom (100 ml.), extract with three 100 ml. portions of water, then dry the chloroform solution over magnesium sulfate and evaporate in vacuo to a residue comprising trans-7-chloro-4-(4'-chlorobenzyloxy)-3-(1''-imidazolylmethyl)thiochroman.

C. In the procedure of each of Examples 2A and 2B replace p-chlorobenzyl chloride in an equivalent quantity of 2-chloro-3-thenyl bromide to obtain, respectively, cis-7-chloro-4-(2'-chloro-3'-thenyloxy)-3-(1''-imidazolylmethyl)thiochroman, and trans-7-chloro-4-(2'-chloro-3'-thenyloxy)-3-(1''-imidazolylmethyl)-thiochroman.

D. Treat each of the 3-(1'-imidazolylmethyl)thiochroman-4-ols prepared in Preparation 2B with p-chlorobenzyl chloride in the manner of Examples 2A and 2B or with 2,5-dichloro-3-thenyl bromide in the manner of Example 2C to obtain, respectively, cis-4-(4'-chlorobenzyloxy)-3-(1''-imidazolylmethyl)thiochroman;
cis-4-(2'-chloro-3'-thenyloxy)-3-(1''-imidazolylmethyl)thiochroman;
cis-6-chloro-4-(4'-chlorobenzyloxy)-3-(1''-imidazolylmethyl)thiochroman;
cis-6-chloro-4-(2'-chloro-3'-thenyloxy)-3-(1''-imidazolylmethyl)thiochroman;
cis-8-chloro-4-(4'-chlorobenzyloxy)-3-(1''-imidazolylmethyl)thiochroman;
cis-8-chloro-4-(2'-chloro-3'-thenyloxy)-3-(1''-imidazolylmethyl)thiochroman;
cis-5,7-dichloro-4-(4'-chlorobenzyloxy)-3-(1''-imidazolylmethyl)thiochroman;
cis-5,7-dichloro-4-(2'-chloro-3'-thenyloxy)-3-(1''-imidazolylmethyl)thiochrioman;
cis-6,7-dichloro-4-(4'-chlorobenzyloxy)-3-(1''-imidazolylmethyl)thiochroman;
cis-6,7-dichloro-4-(2'-chloro-3'-thenyloxy)-3-(1''-imidazolylmethyl)thiochroman;
cis-6,8-dichloro-4-(4'-chlorobenzyloxy)-3-(1''-imidazolylmethyl)thiochroman;
cis-6,8-dichloro-4-(2'-chloro-3'-thenyloxy)-3-(1''-imidazolylmethyl)thiochroman;
cis-7-trifluoromethyl-4-(4'-chlorobenzyloxy)-3-(1''-imidazolylmethyl)thiochroman;
cis-7-trifluoromethyl-4-(2'-chloro-3'-thenyloxy)-3-(1''-imidazolylmethyl)thiochroman;

and the corresponding trans-isomer of each of the foregoing.

F. Treat each of the 3-(1'-imidazolylmethyl)thiochroman-4-ols prepared in Preparation 2B in the manner of Examples 2A and 2B except that in place of p-chlorobenzyl chloride utilize an equivalent quantity of each of the following reagents:
2,5-dichloro-3-thenyl bromide,
2,4-dichlorobenzyl chloride,
2,6-dichlorobenzyl chloride, to obtain, respectively,
(a)(1) cis-4-(2',5'-dichloro-3'-thenyloxy)-3-(1''-imidazolylmethyl)thiochroman;
(2) cis-4-(2',4'-dichlorobenzyloxy)-3-(1''-imidazolylmethyl)thiochroman;
(3) cis-4-(2',6'-dichlorobenzyloxy)-3-(1''-imidazolylmethyl)-thiochroman;
(b)(1) cis-6-chloro-4-(2',5'-dichloro-3'-thenyloxy)-3-(1''-imidazolylmethyl)thiochroman;
(2) cis-6-chloro-4-(2',4'-dichlorobenzyloxy)-3-(1''-imidazolylmethyl)thiochroman;
(3) cis-6-chloro-4-(2',6'-dichlorobenzyloxy)-3-(1''-imidazolylmethyl)thiochroman;
(c)(1) cis-8-chloro-4-(2',5'-dichloro-3'-thenyloxy)-3-(1''-imidazolylmethyl)thiochroman;
(2) cis-8-chloro-4-(2',4'-dichlorobenzyloxy)-3-(1''-imidazolylmethyl)thiochroman;
(3) cis-8-chloro-4-(2',6'-dichlorobenzyloxy)-3-(1''-imidazolylmethyl)thiochroman;
(d)(1) cis-5,7-dichloro-4-(2',5'-dichloro-3'-thenyloxy)-3-(1''-imidazolylmethyl)thiochroman;
(2) cis-5,7-dichloro-4-(2',4'-dichlorobenzyloxy)-3-(1''-imidazolylmethyl)thiochroman;
(3) cis-5,7-dichloro-4-(2',6'-dichlorobenzyloxy)-3-(1''-imidazolylmethyl)thiochroman;
(e)(1) cis-6,7-dichloro-4-(2',5'-dichloro-3'-thenyloxy)-3-(1''-imidazolylmethyl)thiochroman;
(2) cis-6,7-dichloro-4-(2',4'-dichlorobenzyloxy)-3-(1''-imidazolylmethyl)thiochroman;
(3) cis-6,7-dichloro-4-(2',6'-dichlorobenzyloxy)-3-(1''-imidazolylmethyl)thiochroman;
(f)(1) cis-6,8-dichloro-4-(2',5'-dichloro-3'-thenyloxy)-3-(1''-imidazolylmethyl)thiochroman;
(2) cis-6,8-dichloro-4-(2',4'-dichlorobenzyloxy)-3-(1''-imidazolylmethyl)thiochroman;
(3) cis-6,8-dichloro-4-(2',6'-dichlorobenzyloxy)-3-(1''-imidazolylmethyl)thiochroman;
(g)(1) cis-7-trifluoromethyl-4-(2',5'-dichloro-3'-thenyloxy)-3-(1''-imidazolylmethyl)thiochroman;
(2) cis-7-trifluoromethyl-4-(2',4'-dichlorobenzyloxy)-3-(1''-imidazolylmethyl)thiochroman;
(3) cis-7-trifluoromethyl-4-(2',6'-dichlorobenzyloxy)-3-(1''-imidazolylmethyl)thiochroman, and the corresponding trans-isomers of the foregoing.

EXAMPLE 3

CIS-5-CHLORO-3[2'-(4''-(1'''-ACETYL-4'''-PIPERAZINYL)PHENOXY)ETHOXY]-2,3-DIHYDRO-2-(1''''-IMIDAZOLYL METHYL)BENZO(d)THIOPHENE (A) Stir a mixture of cis-5-chloro-2,3-dihydro-3-hydroxy-2-(1'-imidazolylmethyl)benzo(b)thiophene (0.50 gms., 1.87 mmols) and potassium hydroxide (0.15 gms., 2.2 mmols) in acetone (10 ml.) at room temperature for one hour. Add 1-((4'-(1''-acetyl-4''-piperazinyl))phenoxy)-2-bromoethane and stir overnight at room temperature. Add a second portion of potassium hydroxide (0.15 gms., 2.2 mmols) and stir overnight; repeat a third time. Pour the mixture into chloroform (500 ml.) and extract with water (500 ml.). Dry the chloroform solution over anhydrous magnesium sulfate and evaporate in vacuo. Chromatograph the resultant residue on silica gel eluting with 2% methanol in chloroform. Combine the like fractions as determined by thin layer chromatography and evaporate the combined like eluates to give cis-5-chloro-3-[2'-(4''-(1'''-acetyl-4'''-piperazinyl)phenoxy)ethoxy]2,3-dihydro-2-(1''''-imidazolylmethyl)benzo(b)thiophene. (B) Dissolve the product of Step A in a mixture of chloroform (10 ml.) and methanol (10 ml.), acidify to pH 2–3 with hydrochloric acid/2-propanol, and evaporate to a residue comprising cis-5-chloro-3-[2'-(4''-(1''''-acetyl-4'''-piperazinyl)phenoxy)-ethoxy]-2,3,-dihydro-2-(1''''-imidazolylmethyl)benzo(b)thiophene dihydrochloride.

EXAMPLE 4

3-CHLOROTHENYLOXY(OR CHLOROBENZYLOXY)-2,3-DIHYDRO-2-(1''-IMIDAZOLYLMETHYL)BENZO(b)THIOPHENE-1-OXIDES (A)
6-Chloro-3-(2',4'-Dichlorobenzyloxy)-2,3,-Dihydro-2-(1''-Imidazolylmethyl)Benzo(b)Thiophene-1-Oxide To a solution of 6-chloro-3-(2',4'-dichlorobenzyloxy)-2,3-dihydro-2-(1''-imidazolylmethyl)benzo(b)thiophene (0.20 gms., 0.5 mmols) in dichloromethane (10 ml.) cooled to 0°–5° C., add m-chloroperbenzoic acid (0.0812 gms., 0.47 mmols) and stir for one hour. Add sodium sulfite (0.05 gms., 0.40 mmols) and stir for another 30 minutes. Add dichloromethane (25 ml.) to the solution and extract with 10% aqueous sodium carbonate (25 ml.). Dry the organic phase over anhydrous magnesium sulfate and evaporate. Chromatograph the resultant residue on silica gel eluting with 5% methanol in chloroform. Combine like fractions as determined by thin layer chromotography and evaporate the combined eluates to give 6-chloro-3-(2',4'-dichlorobenzyloxy)-2,3-dihydro-2-(1''-imidazolylmethyl)-benzo(b)thiophene-1-oxide, m.p. 60° C.

(B) Treat each of the cis-3-chlorothenyloxy (or chlorobenzyloxy)2,3-dihydro-2-(1''-imidazolylmethyl)benzo(b)thiophenes of Example 1, the 4-chlorobenzyloxy (or chlorothenyloxy)-3-(1''-imidazolylmethyl)thiochromans of Example 2, and the cis-3-[2'-(4''-(1'''-acetyl-4''-piperazinyl)phenoxy)ethoxy]-2,3-dihydro-2-(1''''-imidazlylmethyl)benzo(b)thiophenes of Example 3 in a manner similar to that of Example 4A to obtain the corresponding 1-oxides.

EXAMPLE 5

3-CHLOROTHENYLOXY(OR CHLOROBENZYLOXY)-2,3-DIHYDRO-2-(1''-IMIDAZOLYLMETHYL)BENZO(b)THIOPHENE-1,1-DIOXIDES (A)
6-Chloro-3-(2',4'-Dichlorobenzyloxy)-2,3-Dihydro-2-(1''-Imidazolylmethyl)Benzo(d)Thiophene-1,1-Dioxide To a solution of 6-chloro-3-(2',4'-dichlorobenzyloxy)-2,3-dihydro-2-(1''-imidazolylmethyl)benzo(b)thiophene (0.20 gms., 0.5 mmols) in dichloromethane (10 ml.) cooled to 0°–5° C., add m-chloroperbenzoic acid (0.1624 gms., 0.94 mmols) and stir for one hour. Warm the solution to room temperature and stir overnight. Add dichloromethane (25 ml.) and extract with 105 aqueous sodium carbonate (25 ml.). Dry the organic phase over anhydrous magnesium sulfate and evaporate to give a residue comprising 6-chloro-3-(2',4'-dichlorobenzyloxy)-2,3-dihydro-2-(1''-imidazolylmethyl)benzo(b)thiophene-1,1-dioxide, m.p. 182° C.

(B) Treat each of the cis-3-chlorothenyl (or chlorobenzyloxy)-2,3-dihydro-2-(1''-imidazolylmethyl)benzo(b)thiophenes of Example 1, the 4-chlorobenzyloxy (or chlorophenyloxy)-P3-(1''-imidazolylmethyl)thiochromans of Example 2, and the cis-3-[2'-(4''-(1'''-acetyl-4''''-piperazinyl)phenoxy)ethoxy]-2,3-dihydro-2-(1''''-imidazolylmethyl)benzo(b)thiophenes of Example 3 in a manner similar to that of Example 5A to obtain the corresponding 1,1-dioxides.

EXAMPLE 6

CIS-7-CHLORO-3-(METHYLTHIOMETHOXY)-2,3-DIHYDRO-2-(1'-IMIDAZOLYLMETHYL)-BENZO(b)THIOPHENE

To a suspension of cis-7-chloro-3-hydroxy-2,3-dihydro-2-(1'-imidazolylmethyl)benzo(b)thiophene (2.67 gms., 10 mmols) in dry dimethylformamide (30 ml.) at 0°–5° C., add sodium hydride (50% oil dispersion) (0.53 gms., 11 mmols) and stir for one hour at room temperature. Add chloromethyl methyl sulfide (1.06 gms., 11 mmols) and stir again for one hour at room temperature. Pour the reaction mixture into ether (500 ml.) and extract with three portions (500 ml. each) of water. Dry the ether solution over anhydrous magnesium sulfate and evaporate in vacuo. Chromatograph the resultant residue by high pressure liquid chromatography using two silica gel cartridges and eluting with ethyl acetate. Combine the like eluates as determined by thin layer chromatography and evaporate the combined residues to give cis-7-chloro-3-(methylthiomethoxy)-2,3-dihydro-2-(1'-imidazolylmethyl)benzo(b)-thiophene.

EXAMPLE 7

CIS-6-CHLORO-3-(2'-CHLORO-5'-THENYLOXY)-2,3-DIHYDRO-2-(1''-IMIDAZOLYLMETHYL)-BENZO(b)THIOPHENE

To a solution of cis-6-chloro-2,3-dihydro-3-hydroxy-2-(1'-imidazolylmethyl)benzo(b)thiophene (2.67 gms., 10 mmols) in dry dimethylformamide (27 ml.) at 0°–5° C., add sodium hydride (50% oil dispersion) (0.53 gms., 11 mmols) and stir for one hour at room temperature. Add 2-chloro-5-thenylbromide (2.33 gms., 11 mmol.) and stir again for one hour at room temperature. Pour the reaction mixture into ether (1 l.) and extract three portions (1 l. each) of water. Dry the ether solution over anhydrous magnesium sulfate and evaporate in vacuo. Chromatograph the resultant residue on silica gel eluting with chloroform. Combine the like fractions as determined by thin layer chromatography, evaporate in vacuo and recrystallize the resultant residue from cyclohexane to give cis-6-chloro-3-(2'-chloro-5'-thenyloxy)-2,3-dihydro-2-(1''-imidazolylmethyl)benzo(b)thiophene, m.p. 94°–95° C.

EXAMPLE 8

5-CHLORO-3-(2'-CHLORO-3'-THENYLOXY)-2,3-DIHYDRO-2-(1''-IMIDAZOLYLMETHYL)BENZO(b)FURAN

To a solution of 5-chloro-2,3-dihydro-3-hydroxy-2-(1'-imidazolylmethyl)benzo(b)furan (4.00 gms., 8.3 mmols) in dry dimethylformamide (40 ml.) cooled to 0°–5° C., add sodium hydride (50% dispersion, 0.44 gms., 9.1 mmols) and stir at room temperature for one hour. Add 2-chloro-3-thenylbromide (1.93 gms., 9.1 mmols) and stir at room temperature for another hour. Pour the reaction mixture into ether (500 ml.) and extract with three 500 ml. portions of water. Dry the ether solution over anhydrous magnesium sulfate, filter and evaporate in vacuo to give 5-chloro-3-(2'-chloro-3'-thenyloxy)-2,3-dihydro-2-(1''-imidazolylmethyl)benzo(b)furan.

EXAMPLE 9

CIS-3-(3'-THENYLOXY)-2,3-DIHYDRO-2-(1'-IMIDAZOLYLMETHYL)BENZO(b)THIOPHENES (A) In the procedure of Example 1A, substitute for 2-chloro-3-thenylbromide an equivalent quantity of 3-thenylbromide to obtain cis-6-chloro-3-(3'-thenyloxy)-2,3-dihydro-2-(1''-imidazolylmethyl)benzo(b)thiophene.

(B) In a similar manner, treat each of the cis-2,3-dihydro-3-hydroxy-2-(1'-imidazolylmethyl)benzo(b)thiophenes of Preparations 1B and 5 with 3-thenylbromide to obtain, respectively:
(a) cis-3-(3'-thenyloxy)-2,3-dihydro-2-(1''-imidazolylmethyl)-benzo(b)thiophene,
(b) cis-5-chloro-3-(3'-thenyloxy)-2,3-dihydro-2-(1''-imidazolylmethyl)benzo(b)thiophene,
(c) cis-7-chloro-3-(3'-thenyloxy)-2,3-dihydro-2-(1''-imidazolylmethyl)benzo(b)thiophene,
(d) cis-4,6-dichloro-3-(3'-thenyloxy)-2,3-dihydro-2-(1''-imidazolylmethyl)benzo(b)thiophene,
(e) cis-5,6-dichloro-3-(3'-thenyloxy)-2,3-dihydro-2-(1''-imidazolylmethyl)benzo(b)thiophene,
(f) cis-5,7-dichloro-3-(3'-thenyloxy)-2,3-dihydro-2-(1''-imidazolylmethyl)benzo(b)thiophene, (g) cis-6-trifluoromethyl-3-(3'-thenyloxy)-2,3-dihydro-2-(1''-imidazolylmethyl)benzo(b)thiophene,
(h) cis-6-fluoro-3-(3'-thenyloxy)-2,3-dihydro-2-(1''-imidazolylmethyl)benzo(b)thiophene,
(i) cis-7-fluoro-3-(3'-thenyloxy)-2,3-dihydro-2-(1''-imidazolylmethyl)benzo(b)thiophene.

EXAMPLE 10

CIS-6-CHLORO-3-(3'-PICOLYLOXY)-2,3-DIHYDRO-2-(1''-IMIDAZOLYLMETHYL)BENZO(b)-THIOPHENE AND THE HYDROCHLORIDE THEREOF (A) Dissolve cis-6-chloro-2,3-dihydro-3-hydroxy-2-(1'-imidazolylmethyl)benzo(b)thiophene (4.00 gms., 15.0 mmols) in dry dimethylformamide (40 ml.) cooled to 0°–5° C., add sodium hydride (50% dispersion, 1.51 gms., 31.5 mmols) and stir for one hour at room temperature. Add 3-picolyl chloride hydrochloride (2.71 gms., 16.5 mmols) and stir another hour at room temperature. Pour the reaction mixture into chloroform (1 liter) and extract with four 1 liter portions of water. Dry the chloroform over anhydrous magnesium sulfate, filter and evaporate in vacuo. Chromatograph the resultant residue on silica gel, eluting with 1% methanol in chloroform with 2 ml. of concentrated ammonium hydroxide added for each liter of eluent. Combine the like fractions as determined by thin layer chromatography and evaporate the solution to a residue comprising cis-6-chloro-3-(3'-picolyloxy)-2,3-dihydro-2-(1''-imidazolylmethyl)benzo(b)thiophene, a gum.

Dissolve the above product in a mixture of anhydrous ether (500 ml.) and 2-propanol (10 ml.). Add dropwise a saturated solution of HCl gas in 2-propanol until precipitation is complete. Filter the solution and dry the resultant residue. Redissolve the solid in water and lyophilize to give cis-6-chloro-3-(3'-picolyloxy)-2,3-dihydro-2-(1''-imidazolylmethyl)benzo(b)thiophene dihydrochloride.

EXAMPLE 11

CIS-6-CHLORO-3-(2'-CHLORO-3'-THENYLOXY)-2,3-DIHYDRO-2-(1''-IMIDAZOLYLMETHYL)-BENZO(b)THIOPHENE HYDROCHLORIDE

Dissolve cis-6-chloro-3-(2'-chloro-3'-thenyloxy)-2,3-dihydro-2-(1''-imidazolylmethyl)benzo(b)thiophene (2.0 gms.) in anhydrous ether (400 ml.). Add dropwise a saturated solution of HCl gas in 2-propanol until precipitation is complete, filter and dry the resultant residue to obtain the title compound.

The products of Example 1 and 10 may be treated in a similar manner to obtain the corresponding hydrochloride acid addition salts.

We claim:
1. A compound selected from the group consisting of a compound defined by formula:

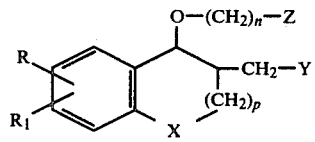

wherein
n is 0 to 4;
p is 0 or 1;

R and $R_1$ are independently H, lower alkyl, halogen, halogenated lower alkyl, nitro, or amino;

X is oxygen, sulfur, sulfinyl, or sulfonyl;

Y is imidazole, or lower alkyl and aryl derivatives of the foregoing, said aryl being a member selected from the group consisting of phenyl, halophenyl, and loweralkylphenyl;

Z is a member selected from the group consisting of alkyl of 1 to 10 carbons, alkenyl of 3 to 10 carbons, alkynyl, of 3 to 10 carbons, cycloalkyl of 3 to 6 carbons, and heterocyclic aromatic groups selected from the group consisting of 2-thienyl, 3-thienyl, pyridyl, quinolyl, thiazolyl and furanyl, and the lower alkyl and halogen substituted derivatives thereof, provided that when n is 0, Z is not 1-alkynyl; and where n is 1 to 4, Z is also a member selected from the group consisting of phenyl, phenyl substituted by lower alkyl, halogen, or N-(N'-lower alkanoyl-piperazine), alkoxy of 1 to 10 carbons, alkylthio of 1 to 10 carbons, aryloxy, and arylthio, wherein said aryl moiety is a member selected from the group consisting of phenyl, halophenyl and lower alkyl phenyl;

and the pharmaceutically acceptable acid addition salts thereof.

2. A compound of claim 1 wherein X is S.
3. A compound of claim 1 wherein p is 0.
4. A compound of claim 1 wherein Y is imidazole.
5. A compound of claim 1 wherein Z is a heterocyclic aromatic group.
6. A compound of claim 2 wherein p is 0.
7. A compound of claim 2 wherein p is 0 and Y is imidazole.
8. The cis-isomer of a compound of claim 2 wherein p is 0 and Y is imidazole, having the formula:

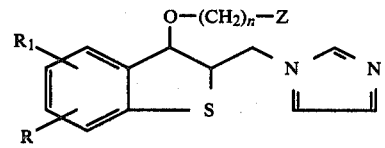

wherein R, $R_1$, Z and n are as defined in claim 1.

9. A compound of claim 8 wherein Z is a heterocyclic aromatic group.
10. A compound of claim 8 wherein R is H, $R_1$ is 6-chloro, n is 1, and Z is 2-chloro-3-thienyl, said compound being cis-6-chloro-3-(2'-chloro-3'-thenyloxy)-2,3-dihydro-2-(1''-imidazolylmethyl)benzo(b)thiophene.
11. A compound of claim 8 wherein R is H, $R_1$ is 6-chloro, n is 1, and Z is 3-thienyl, said compound being cis-6-chloro-3-(3'-thenyloxy)-2,3-dihydro-2-(1''-imidazolylmethyl)benzo(b)thiophene.
12. A compound of claim 8 wherein R is H, $R_1$ is 6-fluoro, n is 1 and Z is 2-chloro-3-thienyl, said compound being cis-6-fluoro-3-(2'-chloro-3'-thenyloxy)-2,3-dihydro-2-(1''-imidazolylmethyl)benzo(b)thiophene.
13. A compound of claim 8 wherein R is H, $R_1$ is 5-fluoro, n is 1, and Z is 2-chloro-3-thienyl, said compound being cis-5-fluoro-3-(2'-chloro-3'-thenyloxy)-2,3-dihydro-2-(1''-imidazolylmethyl)benzo(b)thiophene.
14. A compound of claim 8 where n is 1, Z is 15. A composition useful for inhibiting the growth of fungi, bacteria or protozoa which comprises an antifungally, antibacterially, or antiprotozoally effective amount of a compound of claim 1 in admixture with a carrier.

16. The composition of claim 15 suitable for pharmaceutical use wherein the carrier is a pharmaceutically acceptable, non-toxic carrier.

17. The composition of claim 16 which comprises an antifungally, antibaterially, or antiprotozoally effective amount of the compound of claim 8 together with a pharmaceutically acceptable non-toxic carrier.

18. The composition of claim 17 which comprises an antifungally effective amount of the compound of claim 8 together with a pharmaceutically acceptable non-toxic topical carrier.

19. The composition of claim 18 which comprises an antifungally effective amount of the compound of claim 8 together with a pharmaceutically acceptable non-toxic oral or parenteral carrier.

20. A method of inhibiting the growth of fungi, bacteria, or protozoa which comprises subjecting a host object containing or subject to attack by fungi, bacteria, or protozoa to an antifungally, antibacterially, or antiprotozoally effective amount of a compound of claim 1.

21. The method of claim 20 wherein the compound is administered topically.

22. The method of claim 20 which comprises administering to the host an antifungally, antibacterially, or antiprotozoally effective amount of the compound of claim 8 together with a pharmaceutically acceptable non-toxic carrier.

23. The method of claim 22 which comprises administering an antifungally effective amount of a compound of claim 8 wherein the compound is administered topically.

24. The method of claim 22 which comprises administering an antifungally effective amount of a compound of claim 8 wherein the compound is administered orally or parenterally.

* * * * *

UNITED STATES PATENT AND TRADEMARK OFFICE
CERTIFICATE OF CORRECTION

PATENT NO. : 4,352,808
DATED : October 5, 1982
INVENTOR(S) : Dinanath F. Rane et al.

It is certified that error appears in the above—identified patent and that said Letters Patent is hereby corrected as shown below:

In claim 14, column 23, line 7, following the formulas, add "and R and $R_1$ are H."

Signed and Sealed this

Fourteenth Day of December 1982

[SEAL]

Attest:

GERALD J. MOSSINGHOFF

*Attesting Officer*     *Commissioner of Patents and Trademarks*